(12) United States Patent
Pak et al.

(10) Patent No.: US 6,287,607 B2
(45) Date of Patent: *Sep. 11, 2001

(54) POTASSIUM CALCIUM CITRATE COMPOSITIONS AND METHODS THEREFOR

(75) Inventors: Charles Y. C. Pak, Dallas; George Alexandrides; Neill B. Walsdorf, both of San Antonio, all of TX (US)

(73) Assignees: Mission Pharmacal Company, San Antonio; Board of Regents, University of Texas System, Austin, both of TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/356,649

(22) Filed: Jul. 19, 1999

(51) Int. Cl.$^7$ .................. A61K 33/06; A61K 31/194; A61K 33/00

(52) U.S. Cl. .................. 424/682; 424/686; 424/687; 424/688; 424/693; 424/715; 424/717; 424/722; 514/553; 514/557; 514/574

(58) Field of Search .................. 424/682, 686, 424/687, 688, 693, 715, 717, 722; 514/553, 557, 574

(56) References Cited

U.S. PATENT DOCUMENTS

| | | | |
|---|---|---|---|
| 4,772,467 | 9/1988 | Pak | 424/602 |
| 4,814,177 | 3/1989 | Walsdorf et al. | 424/464 |
| 4,851,221 | 7/1989 | Pak et al. | 424/693 |
| 4,895,980 | 1/1990 | Walsdorf et al. | 562/584 |
| 4,985,593 | 1/1991 | Walsdorf et al. | 562/584 |
| 5,075,499 | 12/1991 | Walsdorf et al. | 562/590 |
| 5,204,134 | 4/1993 | Girsh | 426/580 |
| 5,213,838 | 5/1993 | Sheikh | 426/649 |
| 5,219,889 | 6/1993 | Walsdorf et al. | 514/574 |
| 5,432,200 | 7/1995 | Walsdorf et al. | 514/574 |

FOREIGN PATENT DOCUMENTS

| | | |
|---|---|---|
| 0 673 913 A1 | 3/1995 | (DE) . |
| 0 673 913 * | 3/1995 | (EP) . |
| 0 702 954 A2 | 3/1996 | (EP) . |
| 0 875 153 A2 | 11/1998 | (EP) . |
| WO 99/51114 | 10/1999 | (WO) . |

OTHER PUBLICATIONS

Barzel, U.S., "The Skeleton as an Ion Exchange System: Implications for the Role of Acid–Base Imbalance in the Genesis of Osteoporosis," *Journal of Bone and Mineral Research*, 10(10):1431–1436, 1995.

Dawson–Hughes, et al., "A Controlled Trial of the Effect of Calcium Supplementation on Bone Density in Postmenopausal Women,"*New England Journal of Medicine*, 333(13):878–883, Sep. 1990.

Harvey, et al., "Superior Calcium Absorption From Calcium Citrate than Calcium Carbonate Using External Forearm Counting," *Journal of the Amer. College of Nutrition*, 9(6):583–857, 1990.

Harvey, et al., "Reduced Propensity For the Crystallization of Calcium Oxalate in Urine Resulting From Induced Hypercalciuria of Calcium Supplementation," *Journal of Clinical endocrinology and Metabolism*, 61(6):1223–1225, Jul. 1985.

Kraut, et al., "Bone, Acid, and Osteoporosis," *New England Journal of Medicine*, 330(25):1821–1822, Jun. 1994.

Lemann, Jr., et al., "Potassium Bicarbonate, But Not sodium Bicarbonate, Reduces Urinary Calcium Excretion and Improves Calcium Balance in Healthy Men," *Kidney International*, 35:688–695, 1989.

Lemann, J., "Urinary Calcium Excretion and Net Acid Excretion: Effects of Dietary Protein, Carbohydrate and Calories," in Urolithiasis and Related Clinical Research, P.O. Schwille LH et al. (Ed.),Plenum Press 1985.

McKane, et al., "Role of Calcium Intake in Modulating Age–Related Increases in Parathyroid Function and Bone Resorption," *Journal of Clinical Endocrinology and Metabolism*, 81(5):1699–1703, 1996.

Morris, Jr., et al., "Potassium Bicarbonate Has Greater Antihypertensive Potency Than Potassium Chloride in Patients With Essential Hypertension," *Journal of the Amer. Soc. of Nephrology*, 3(3):533, Sep. 1992.

Oh, M.S., "A New Method for Estimating G–I Absorption of Alkali," *Kidney International*, 36:915–917, 1989.

Pak, et al., "Idiopathic Hypocitraturic Calcium–Oxalate nephrolithiasis Successfully Treated With Potassium Citrate," *Annals of Internal Medicine*, 104(1):33–37, 1986.

Pietschmann, et al., "Reduced Vertebral Bone Density in Hypercalciuric Nephrolithiasis," *Journal of Bone and Mineral Research*, 7(12):1383–1388, 1992.

Sakhaee, et al., "Limited Risk of Kidney Stone Formation During Long–Term Calcium Citrate Supplementation in Nonstone Forming Subjects," *Journal of Urology*, 152:324–327, Aug. 1984.

Sakhaee, et al., "citraturic Response to Oral Citric Acid Load," *Journal of Urology*, 147:975–876, Apr. 1992.

(List continued on next page.)

*Primary Examiner*—Jose' G. Dees
*Assistant Examiner*—Frank Choi
(74) *Attorney, Agent, or Firm*—Charles W. Hanor (57) ABSTRACT

A composition useful as a dietary supplement for providing potassium, calcium, and citrate is presented, as well as processes for producing the composition, and methods for using the composition as a dietary supplement. Administration of the composition counters bone loss associated with aging or menopause by providing bioavailable calcium and, simultaneously, delivering alkali load. In addition, administration of the composition produces a substantial increase in urinary citrate, which counters kidney-stone formation.

44 Claims, 7 Drawing Sheets

OTHER PUBLICATIONS

Sebastian, et al., "Improved Mineral Balance and Skeletal Metabolism in Postmenopausal Women Treated With Potassium Bicarbonate," *New England Journal of Medicine,* 330(25):1776–1781, Jun. 1994.

Rudnic, et al., "Oral Solid Dosage Forms," in Remington: The Science and Practice of Pharmacy, Gennaro, AR (ed.), Mack Publ. Co., Easton, PA, pp. 1615–1649, 1995.

* cited by examiner

POTASSIUM CALCIUM CITRATE COMPOSITIONS AND METHODS THEREFOR

FIELD OF THE INVENTION

The present invention relates to a composition comprising high bulk density potassium calcium citrate as a single compound, wherein the molar ratio of potassium to calcium to citrate in the single compound is 1:1:1, or 4:1:2, respectively. The present invention also relates to processes for producing the composition in a solid form having a bulk density from about 0.8 g/cc to about 1.3 g/cc, as well as methods for using the composition as a dietary supplement, for example, to counter bone loss while avoiding kidney-stone formation.

BACKGROUND OF THE INVENTION

Mineral compositions are commonly taken as dietary aids, either as therapeutic preparations directed to a specific medical problem or as general nutritional supplements. Among useful dietary supplements are dosage units of calcium citrate, orally administered in solid or liquid form (U.S. Pat. Nos. 4,772,467, 4,814,177, and 4,851,221; each patent herein incorporated by reference). Oral administration of calcium citrate as a nutritional supplement both modestly increases levels of urinary citrate and provides bioavailable calcium. By modestly increasing levels of urinary citrate, administration of calcium citrate counters calcium nephrolithiasis (i.e., formation of calcium-containing kidney stones). Furthermore, calcium is more readily absorbed when administered as calcium citrate than as calcium carbonate, i.e., the administration of calcium citrate provides calcium that is more bioavailable. Improved absorption of calcium allows more effective treatment of calcium-deficiency conditions like osteoporosis.

Osteoporosis—a condition in which an affected person's bones become increasingly porous, brittle, and subject to fracture, owing to loss of calcium and other mineral components— is common in older persons, particularly in postmenopausal women. Bone loss may also be associated with a variety of other conditions, including those brought on by long-term steroid therapy and certain endocrine disorders. If not countered, osteoporosis or bone loss may lead to fractures of the spine, hip, and long bones.

Certain drugs that block bone destruction may help avert the progression of postmenopausal osteoporosis. The most potent of these drugs are found among a class of synthetic compounds called bisphosphonates. Alendronate (4-amino-1-hydroxybutylidene-1,1-bisphosphonic acid), which is approved by the Food and Drug Administration (FDA) for treatment of osteoporosis, has been shown to produce a transient increase in spine and hip bone density, as well as to reduce spinal fractures. Alendronate's long-term effects are not known, however, and it may cause esophageal ulcers. Estrogen replacement therapy has shown effectiveness in countering postmenopausal osteoporosis. However, estrogen may increase the risk of breast cancer, and may cause discomforting side effects, such as vaginal bleeding, if it is given intermittently with progesterone, which is usually recommended. Estrogen analogs may overcome some of the side effects of estrogen, but cause others, such as hot flashes and blood clots.

Intake of calcium offers potentially a safer and more natural means of averting postmenopausal osteoporosis. Both the FDA and the National Institutes of Health have endorsed adequate intake of calcium as a means of countering the bone loss that occurs with menopause in women, and with aging in both men and women.

Calcium's action in countering bone loss has been ascribed to its ability to suppress secretion of parathyroid hormone (PTH), a hormone that stimulates bone resorption or destruction (e.g., see McKane, WR et al., 1996, *J. Clin. Endocrin. & Metab.* 81:1699–1703). Moreover, calcium ensures adequate mineralization of bone by providing an essential component of bone. The average weight percent of calcium in the human body is approximately 1.4, and approximately 99 percent of calcium in the human body is found in skeletal structures. Consistent with these facts, supplementation of the diet with calcium can be an important element of preventing and treating osteoporosis, as well as bone loss associated with other pathologies, such as chronic diarrheal syndrome. Supplementation of diet with calcium may also be an important element of treating other conditions, including hypoparathyroidism, renal osteodystrophy, hypertension, and phosphate accumulation in chronic renal failure.

The use of dietary supplements that provide calcium, however, has limitations. For example, the amount of calcium absorbed from supplements taken daily tends to decline with time (e.g., see Sakaee et al., 1994, *J. Urology* 152:324–27). In addition, intake of additional calcium may promote the formation of calcium-containing kidney stones. The risk of such kidney-stone formation (i.e., calcium nephrolithiasis) may be particularly high in patients with hypercalciuria, especially when the hypercalciuria results because of excess calcium absorption from the gastrointestinal (GI) tract (as in absorptive hypercalciuria).

The chemical form in which dietary calcium supplements are administered is of consequence for their capacity to provide bioavailable calcium as well as their propensity to promote kidney-stone formation. As noted previously, when calcium is orally administered as calcium citrate, calcium absorption is greater than when calcium is administered as calcium carbonate (e.g., see Harvey et al., 1990, *J. Am. Coll. of Nutr.*, 9(6):583–587; Dawson-Hughes et al., 1990, *N. Eng. J. Med.* 223:878–83). Not only is calcium more bioavailable when administered as calcium citrate, calcium-citrate administration also has a mild citraturic effect. Administration of calcium as calcium citrate modestly increases the level of urinary citrate, which retards formation of kidney stones (Harvey et al., 1985, *J. Clin. Endocrin. & Metab.* 61:1223–25).

However, supplements other than calcium citrate have greater citraturic effects, including, in order of increasing effectiveness, potassium bicarbonate, potassium citrate, and magnesium potassium citrate. U.S. Pat. Nos. 4,895,980, 4,985,593, 5,219,889 and 5,432,200 (each incorporated herein by reference) relate to compositions of, as well as to methods for making and using, magnesium potassium citrate.

In studies comparing citraturic effects of potassium citrate and potassium bicarbonate, potassium citrate has been shown to produce more prominent levels of urinary citrate than equivalent amounts of potassium bicarbonate (Sakhaee, K. et al., 1992, *J. Urology*, 147:975–976). While the citraturic action of potassium citrate was attributable mostly to its delivery of alkali load, its citraturic action also resulted from renal excretion of absorbed citrate escaping in vivo metabolism. Consequently, oral administration of potassium bicarbonate, because it also delivered alkali load, also had a citraturic effect, but less than that of potassium citrate.

Delivering alkali load is not only a mechanism for inducing a citraturic effect, but it also represents an additional mechanism for countering bone loss (Sebastian A. et al., 1994, *N. Eng. J. Med.*, 330:1776–1781). Thus, potassium citrate, for example, may be administered not only to provide a citraturic effect to counter formation of kidney stones, but also independently to counter bone loss by delivering alkali load. Delivering alkali load counters bone loss by partly compensating for the cumulative buffering effect that skeletal sources provide against diet-dependent acid production (Sebastian A. et al., 1994, *N. Eng. J. Med.*, 330:1776–1781). Age-related reductions in bone mass appear to result at least in part from this cumulative buffering effect. In postmenopausal women, for example, the oral administration of potassium bicarbonate at a dose sufficient to deliver alkali load improves calcium and phosphorus balance, and appears both to reduce bone resorption and to increase the rate of bone formation. As another example, oral administration of potassium bicarbonate, but apparently not sodium bicarbonate, also reduces urinary calcium excretion and improves calcium balance in healthy men (Lemann et al., 1989, *Kidney Int'l* 135:688–695).

Contrasting the calcium-balance effects of potassium bicarbonate with those of sodium bicarbonate indicates that potassium alone, independent of bicarbonate, may trigger a reduction urinary calcium excretion. Consequently, while preliminary in nature, these results indicate that the provision of potassium itself may have a role in countering kidney-stone formation by reducing urinary calcium excretion.

Use of a dietary supplement consisting essentially of calcium and citrate has been recognized both to provide calcium and, as an ancillary benefit, to deliver a small or modest level of alkali load (U.S. Pat. No. 4,851,221, previously incorporated by reference). However, since the alkali load level delivered by a dietary supplement like a calcium citrate generally correlates with cations absorbed, and since absorption of calcium cations from a dietary supplement like a calcium citrate may be relatively small, the alkali load level delivered by a dietary supplement consisting essentially of calcium and citrate is relatively quite modest. Furthermore, since absorption of calcium cations may be attenuated over time, the alkali load level delivered by a dietary supplement consisting essentially of calcium and citrate also may be attenuated over time.

A mineral composition comprising magnesium potassium citrate in a single salt (having a molar ratio of magnesium to potassium to citrate of 1:4:2, respectively) is useful as a dietary supplement to overcome certain renal losses of magnesium and potassium, as well as to increase urinary excretion of electrolytes (U.S. Pat. Nos. 4,895,980, 4,985,593, 5,219,889, and 5,432,200; each previously incorporated by reference). While the mineral composition comprising magnesium potassium citrate in a single salt delivers, as a dietary supplement, a significant level of alkali load, it is not a source of calcium. Furthermore, while the mineral composition provides magnesium, magnesium neither suppresses secretion of PTH nor ensures adequate mineralization of bone. In general, magnesium is not a physiological substitute for calcium. A mineral composition, amenable for administration as a dietary supplement, that simultaneously provides bioavailable calcium and delivers a more-than-modest level of alkali load, while countering kidney-stone formation, is desirable.

| ABBREVIATIONS | |
|---|---|
| DPD: | deoxypyridinoline |
| FDA: | Food and Drug Administration |
| GF: | glomerular filtrate |
| GI: | gastrointestinal |
| meq: | milliequivalents |
| mmol: | millimoles |
| PCC: | potassium calcium citrate |
| PTH: | parathyroid hormone |

SUMMARY OF THE INVENTION

The present invention provides compositions comprising high bulk density potassium calcium citrate (PCC) as a single compound, processes for producing these PCC compositions, and methods for using them as dietary supplements to counter, for example, bone loss while avoiding kidney-stone formation. In addition to alleviating calcium-deficiency conditions, administration of these PCC compositions delivers a more-than-modest level of alkali load. As a result, patients in need of both calcium and alkali load may take one type of supplement rather than two types (i.e., one type to provide calcium and another type to deliver alkali load). Consequently, for patients in need of both calcium and alkali load, the availability of compositions comprising high bulk density PCC as a single compound is particularly beneficial in terms of patient compliance.

Physiological studies, as reported herein, demonstrate that administration of a PCC composition as a dietary supplement, while providing bioavailable calcium, simultaneously delivers alkali load at a level greater than the modest level delivered by a dietary supplement consisting essentially of calcium and citrate (where an equivalent amount of calcium is provided by administration of either supplement). Significant increases in urinary pH on administration of the PCC composition evidence delivery of this level of alkali load. The increases in urinary pH also evidence a means by which administration of a PCC composition counters kidney-stone formation. The physiological studies further demonstrate that administration of the PCC composition provides unexpectedly profound citraturic effects.

Thus, administration of a PCC composition counters kidney-stone formation by increasing urinary pH and by providing unexpectedly profound citraturic effects, as well as, at least potentially, by providing potassium instead of sodium. Consequently, among other advantages conferred, embodiments of the present invention counter bone loss (by both providing calcium and delivering more-than-modest levels of alkali load) and kidney-stone formation (by increasing urinary pH, providing unexpectedly profound citraturic effects, and providing potassium instead of sodium).

By both providing calcium (e.g., at a dose of 0.5–2.0 g calcium per day) and delivering more-than-modest levels of alkali load (while simultaneously countering kidney-stone formation), dietary supplementation with embodiments of the present invention can be an important element of preventing and treating osteoporosis, as well as bone loss associated with other pathologies, such as chronic diarrheal syndrome, osteomalacia, rickets, and renal osteodystrophy. By providing calcium (e.g., at a dose of 0.5–2.0 g calcium per day) (while simultaneously countering kidney-stone formation), dietary supplementation with embodiments of the present invention may also be indicated for treating other medical conditions for which dietary supplementation with calcium may be desireable, including hypoparathyroidism, hypertension, and phosphate accumulation in chronic renal failure. By providing potassium (e.g., at a dose of 20–60 milliequivalents (meq) potassium per day), dietary supplementation with embodiments of the present invention may also be useful for countering certain potassium-deficiency conditions.

In particular, the invention provides a composition useful as a dietary supplement to provide potassium, calcium, and citrate, said composition comprising high bulk density potassium calcium citrate as a single compound, wherein the molar ratio of potassium to calcium to citrate in the single compound is 1:1:1. As used herein, "high bulk density" means a bulk density that is from about 0.8 g/cc to about 1.3 g/cc for a solid form (e.g., a granulated or powdered form) of the PCC composition, after the container (e.g., a graduated cylinder) used to measure the solid form's volume is tapped to settle the solid form within the container. In a related embodiment, the invention provides the composition having a bulk density ranging between about 0.9 g/cc to about 1.3 g/cc, or, more preferably, between about 0.9 g/cc to about 1.1 g/cc. A related embodiment of the invention provides the composition in a unit dosage form that provides about 5 meq potassium, about 10 meq calcium, and about 15 meq citrate in each dosage unit.

Another aspect of the invention provides a composition useful as a dietary supplement to provide potassium, calcium, and citrate, said composition comprising high bulk density potassium calcium citrate as a single compound, wherein the molar ratio of potassium to calcium to citrate in the single compound is 4:1:2, respectively. In a related embodiment, the invention provides the composition having a bulk density ranging between about 0.9 g/cc to about 1.3 g/cc, or, more preferably, between about 0.9 g/cc to about 1.1 g/cc. A related embodiment of the invention provides the composition in a unit dosage form that provides about 10 meq potassium, about 5 meq calcium, and about 15 meq citrate in each dosage unit.

In related embodiments, compositions comprising high bulk density potassium calcium citrate as a single compound and having a moisture content of less than about 5 percent, whether the molar ratio of potassium to calcium to citrate in the single compound is 1:1:1, or 4:1:2, respectively, are also provided by the invention.

Related embodiments of the invention provide a composition comprising high bulk density potassium calcium citrate as a single compound having the chemical formula $KCa(OOCCH_2COHCOOCH_2COO)$, while other embodiments of the invention provide a composition comprising high bulk density potassium calcium citrate as a single compound having the chemical formula $K_4Ca(OOCCH_2COHCOOCH_2COO)_2$.

Depending on the distribution of electrons shared between substituent atoms, chemical bonds joining potassium, calcium, and citrate moieties in a single compound of potassium calcium citrate may vary between being somewhat covalent in nature to being largely ionic in nature, regardless of whether the high bulk density potassium calcium citrate as a single compound has a molar ratio of potassium to calcium to citrate in the single compound of 1:1:1 (or has the chemical formula $KCa(OOCCH_2COHCOOCH_2COO)$) or 4:1:2, respectively (or has the chemical formula $K_4Ca(OOCCH_2COHCOOCH_2COO)_2$). In particular, while binding of potassium and citrate moieties may be largely ionic in nature, binding of calcium and citrate moieties may involve the formation of a chelation complex that can be thought of as including bonds formed through coordination covalency. In solid form, high bulk density potassium calcium citrate occurs as a single compound, in 1:1:1, or 4:1:2, respectively, molar ratio. On dissolving in aqueous solution (e.g., on contact with gastric juices after ingestion of a PCC composition), it is expected, however, to be ionized primarily into potassium ions, calcium ions, and citrate ions (or ions of calcium citrate complexes). Consequently, given its capacity for ionization, such high bulk density potassium calcium citrate as a single compound may also be described as high bulk density potassium calcium citrate in a single salt, wherein the single salt is a dual mineral salt.

In another aspect, the invention provides process for producing a composition having a water content of less than about 5 weight percent, said composition comprising high bulk density potassium calcium citrate as a single compound, wherein potassium, calcium, and citrate in the single compound are in a molar ratio of 1:1:1, the process comprising the steps of: mixing citric acid, a calcium compound, and water to form a first mixture wherein citric acid and calcium are in approximately 1:1 molar ratio; adding a potassium compound to form a second mixture wherein potassium and citric acid are in approximately 1:1 molar ratio and the second mixture has a water content of between about 10 weight percent and about 75 weight percent; and drying and milling said second mixture to a water content of less than about 5 weight percent to produce the composition. In another embodiment, the invention also provides process in which the composition produced by such process has a bulk density between about 0.9 g/cc and about 1.1 g/cc. In other embodiments, compositions produced by such processes are also provided by the invention. In further embodiments, the invention provides such processes wherein the second mixture has a water content of between about 10 weight percent and about 25 weight percent. In further embodiments, the invention provides such processes wherein the calcium compound is selected from the group consisting of calcium oxide, calcium carbonate, calcium hydroxide, and mixtures thereof. In additional embodiments, the invention provides such processes wherein the potassium compound is selected from the group consisting of potassium carbonate, potassium hydroxide, potassium bicarbonate, and mixtures thereof.

In a related aspect, the invention provides a process for producing a composition having a water content of less than about 5 weight percent, said composition comprising high bulk density potassium calcium citrate as a single compound, wherein potassium, calcium, and citrate in the single compound are in a molar ratio of 4:1:2, respectively, the process comprising the steps of: mixing citric acid, a calcium compound, and water to form a first mixture wherein citric acid and calcium are in approximately 2:1 molar ratio, respectively; adding a potassium compound to form a second mixture wherein potassium and citric acid are in approximately 2:1 molar ratio, respectively, and the second mixture has a water content of between about 10 weight percent and about 75 weight percent; and drying and milling said second mixture to a water content of less than about 5 weight percent to produce the composition. In another embodiment, the invention also provides process in which the composition produced by such process has a bulk density between about 0.9 g/cc and about 1.1 g/cc. In other embodiments, compositions produced by such processes are also provided by the invention. In further embodiments, the invention provides such processes wherein the second mixture has a water content of between about 10 weight percent and about 25 weight percent. In further embodiments, the invention provides such processes wherein the calcium compound is selected from the group consisting of calcium oxide, calcium carbonate, calcium hydroxide, and mixtures thereof. In additional embodiments, the invention provides such processes wherein the potassium compound is selected from the group consisting of potassium carbonate, potassium hydroxide, potassium bicarbonate, and mixtures thereof.

A method for providing potassium, calcium, and citrate, and a method for delivering a more-than-modest level of alkali load, to a subject in need thereof, are also provided by the invention, as are a method for countering bone loss, and a method for countering osteoporosis, in subject in need thereof, such methods, in certain embodiments, comprising the step of administering as a dietary supplement to the subject a composition comprising high bulk density potassium calcium citrate as a single compound, the molar ratio of potassium to calcium to citrate in the single compound being either 1:1:1, or 4:1:2, respectively. The subject in need of any of such methods may be a subject susceptible to kidney-stone formation.

Other features and advantages of the invention will be apparent from the following description of the preferred embodiments thereof, and from the claims. Folling long-standing patent law convention, the terms "a" and "an" mean "one or more" when used in this application, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In the drawings, significant-difference levels for treatments of PCC composition or calcium citrate (ULTRADENSE™ CITRACAL®) versus placebo are represented as follows:
($p<0.05$);
($p<0.01$); and,
($p<0.001$).
Lines for different treatments are represented as follows:
PCC composition (●—●);
calcium citrate (△—△); and,
placebo (■—■).
Methodologies of the treatments are detailed in Example 7, infra.

DETAILED DESCRIPTION OF THE PREFERRED EMBODIMENTS

Compositions comprising high bulk density PCC as a single compound are provided by the present invention. High bulk density PCC as a single compound is synthesized by reacting stoichiometric quantities of citric acid, a calcium compound, and a potassium compound. A reaction in which equimolar amounts of potassium, calcium, and citrate are complexed as a single compound may be represented as follows:

While not wanting to be bound by theory, a likely structural formula for this single compound is:

A reaction in which molar amounts of potassium, calcium, and citrate—in a 4:1:2, respectively, molar ratio—are complexed as a single compound may be represented as follows:

While not wanting to be bound by theory, a likely structural formula for this single compound is:

Either reaction is preferably initiated by the slow addition of the calcium compound to a mixture of water and citric acid, followed by the slow introduction of the potassium compound to the reaction mixture.

According to a preferred embodiment of the invention, the calcium compound is selected from the group consisting of calcium carbonate, calcium oxide, calcium hydroxide, and mixtures thereof. Calcium oxide is the preferred calcium compound from a cost standpoint, although the use of calcium carbonate will provide better control over the temperature of the reaction mixture.

The potassium compound is preferably selected from the group consisting of potassium carbonate, potassium hydroxide, potassium bicarbonate, and mixtures thereof. Potassium carbonate is generally preferred because of its lower cost.

Citric acid and water are mixed with agitation, and calcium compound and potassium compound are thereafter sequentially mixed with the citric acid to produce a dense, hydrated second mixture. This dense, hydrated second mixture may be initially characterized as being a thick "slush" comprising potassium, calcium, and citrate in a mole proportion of about 1:1:1, or about 4:1:2, respectively, depending on the molar amounts of reactant compounds used.

During addition of the calcium or potassium compound, the temperature of the mixture is desirably controlled between about 10° C. and about 70° C. by controlling compound addition rates. A preferred temperature range for the reaction mixture is from about 15° C. to about 60° C., with a most preferred temperature range being fiom about 20° C. to about 50° C.

The hydrated second mixture preferably has a moisture content between about 15 weight percent and about 25 weight percent. If the moisture content falls below about 10 weight percent, the reaction likely will be incomplete. While a hydrated second mixture with a moisture content above about 25 weight percent (for example, 50 or 75 weight percent or more) may be used to produce a bulk or granulated composition, more time and/or energy is required to lower the moisture content of the mixture, with the mixture retaining a paste-like consistency for a longer period. The need to use a longer period of time and/or more energy to lower the moisture content of the second mixture is economically disadvantageous.

This hydrated second mixture is thereafter preferably blended in a ribbon mixer to a granular mass consisting of granules and lumps. The mass is then dried and milled to produce a bulk form of PCC composition, i.e., a granulated PCC composition, having a maximum particle size of about 1/16 inch (i.e., about 0.16 cm) in diameter and having a moisture content ranging between about 0 weight percent and about 5 weight percent. The granulated form thus produced has a bulk density (weight or mass per gross volume of granules) ranging from about 0.8 g/cc to about 1.3 g/cc, preferably from about 0.9 g/cc to about 1.3 g/cc, and most preferably from about 0.9 g/cc to about 1.1 g/cc. The granulated form, with or without further milling and sizing, provides pharmaceutically-acceptable material suitable for producing PCC composition in unit dosage form. The granulated form is a preferred precursor for the production of tablets, or other orally-administered forms, of PCC composition. It represents a densified source for providing potassium, calcium, and citrate, as well as for delivering a more-than-modest level of alkali load. Furthermore, the granulated form is compressible, with appropriate tableting aids.

A tablet form of a PCC composition is produced by subjoining and blending a bulk PCC composition, a lubricant such as stearic acid, calcium stearate, magnesium stearate, zinc stearate, talc, mineral oil, or the like, and a wax material such as carnauba wax or polyethylene glycol. In certain embodiments, granulating agents such as ethyl cellulose, povidone, polyethylene glycol, shellac, methyl cellulose, or the like are also added to the blend. In certain embodiments, an aroma enhancer, such as ethyl vanillin, for example, may be included to provide a pleasant aroma. Pharmaceutically-acceptable tableting binders, lubricants, disintegrants, carriers, and excipients known in the pharmaceutical arts in light of the present disclosure are usable in the production of tablets or other solid forms of the present invention (See, e.g., Remington: The Science and Practice of Pharmacy, Gennaro, AR (ed.), 1995, Mack Publ. Co., Easton, Pa., p. 1615, incorporated herein by reference). The resulting compositions are then fed through a multiple-station tablet press. Multiple-station tablet presses such as a Manesty Mark 345 station press, a Fette 45 station press, or a Manesty rotopress-37 station press, for example, may be used, but the formation of tablets of PCC compositions are not limited to such presses.

Preferred tablets of a PCC composition comprising high bulk density potassium calcium citrate as a single compound, in 1:1:1 molar ratio, preferably comprise about 13.4 weight percent potassium, about 13.7 weight percent calcium, and about 64.7 weight percent citrate, with the remaining about 8.2 weight percent being lubricant, wax material, granulating agent, tableting binder, disintegrant, carrier, excipient, or other additive. Preferred tablets of a PCC composition comprising high bulk density potassium calcium citrate as a single compound, in 4:1:2, respectively, molar ratio, preferably comprise about 25.0 weight percent potassium, about 6.4 weight percent calcium, and about 60.4 weight percent citrate, with the remaining about 8.2 weight percent being lubricant, wax material, granulating agent, tableting binder, disintegrant, carrier, excipient, or other additive.

Further processing to improve tablets of a PCC composition physically and aesthetically may be accomplished by tablet-coating procedures well known to those skilled in relevant pharmaceutical arts in light of the present disclosure. For example, a film coating may be added to protect tablet ingredients from moisture, oxygen, or light; or to mask any undesirable taste or appearance. Suitable coating agents include cellulose, hydroxypropylmethyl cellulose, cellulose phthalate, methacrylic copolymer, polyethylene glycol, polyvinylpyrrolidone (PVP), sugar, titanium dioxide, talc, and shellac. An enteric coating may be employed, as well as coloring agents for identification, and, if desired, the solid form may be polished with a waxy composition, such as carnuba wax. Coating procedures are by conventional pharmaceutical pan-coating technology known to those of skill in this art in light of this disclosure.

In a preferred embodiment of the invention, the PCC composition is a composition comprising high bulk density potassium calcium citrate as a single compound in 1:1:1 molar ratio. In an example of this preferred embodiment, the PCC composition is a potent delivery system yielding 5 meq of potassium (about 195 mg), 10 meq of calcium (about 200 mg), and 15 meq of citrate (about 945 mg) from each PCC tablet (about 1.34 g total, excluding lubricants, waxy materials, granulating agents, binders, disintegrants, carriers, excipients, coating materials, or the like). In another preferred embodiment of the invention, the PCC composition is a composition comprising high bulk density potassium calcium citrate as a single compound in 4:1:2, respectively, molar ratio. In an example of this preferred embodiment, the PCC composition is a potent delivery system yielding 10 meq of potassium (about 391 mg), 5 meq of calcium (about 100 mg), and 15 meq of citrate (about 945 mg) from each PCC tablet (about 1.44 g total, excluding lubricants, waxy materials, granulating agents, binders, disintegrants, carriers, excipients, coating materials, or the like).

PCC compositions may be orally administered directly as supplements in tablet or other solid forms, or indirectly after being dissolved in a liquid to produce a beverage form. Solid forms suitable for oral administration include tablets, lozenges, chewable tablets, granules, bulk powder, or the like, as well as capsules containing granules or powder.

As used herein, a composition "delivering alkali load" means that the composition is delivering for absorption through a GI tract mineral cations that are not degraded (though anions are metabolized). As used herein, a "modest level" of alkali load means the level of alkali load delivered on administration of a supplement consisting essentially of calcium and citrate (such as the calcium-citrate supplement of Example 7, infra).

The level of alkali load that is delivered on administration of a PCC composition or a supplement consisting essentially of calcium and citrate correlates with cations absorbed through a GI tract. Because potassium cations are more readily absorbed through a GI tract than calcium cations, the level of alkali load delivered by a PCC composition is greater than a modest level of alkali load, where the calcium content provided by the calcium-citrate supplement that delivers the modest level of alkali load is approximately identical to the calcium content provided by the PCC composition. In other words, administration of PCC composition delivers a more-than-modest level of alkali load.

As used herein, "delivering a more-than-modest level" of alkali load by a PCC composition means delivering a level of alkali load greater than the "modest level" of alkali load delivered by a supplement consisting essentially of calcium and citrate, where the calcium content provided by the calcium-citrate supplement that delivers the modest level of alkali load is approximately identical to the calcium content provided by the PCC composition.

Levels of alkali load delivered are measured by analysis of urinary electrolytes. Measuring alkali load by analysis of urinary electrolytes (in particular, urinary non-combustible anions and urinary non-combustible cations) correlates closely with measuring alkali load by analysis of food and fecal electrolytes (Oh, MS, 1989, *Kidney Int'l* 36:915–17). Subtracting the level of urinary non-combustible anions from the level of urinary non-combustible cations results in a net alkali absorption value. A positive value is generated when the net alkali absorption value provided by a supplement consisting essentially of calcium and citrate is subtracted from the net alkali absorption value provided by a PCC composition, where the amount of calcium administered in the supplements compared is approximately identical. As indicated by the positive value, the level of alkali load corresponding to that delivered by a PCC composition is a more-than-modest level of alkali load. A "calcium load" test as described in Example 7, infra, provides a context for determining net alkali absorption values.

Measuring changes in levels of urinary ammonium may also be used to indicate levels of alkali load delivered. A decline in urinary ammonium is associated with delivering alkali load. In addition, measuring changes in urinary pH levels may be used to indicate levels of alkali load delivered. An increase in urinary pH is associated with delivering alkali load. Measuring changes in levels of urinary ammonium and/or urinary pH may also be used to demonstrate that the level of alkali load corresponding to that delivered by administration as a dietary supplement of a PCC composition is a more-than-modest level of alkali load. A "calcium load" test as described in Example 7, infra, also provides a context for determinations of changes in levels of urinary ammonium and/or urinary pH. As used herein, "increasing urinary pH" and "increasing urinary citrate" are described by the experimental protocol followed in Example 7, infra.

As used herein, "drying and milling said second mixture to a water content of less than about 5 weight percent to produce the composition" includes the meaning that, in drying the second mixture comprising water and high bulk density potassium calcium citrate as a single compound (whether having a molar ratio of potassium to calcium to citrate of either 1:1:1 or 4:1:2, respectively) to a water content of less than about 5 weight percent, intermediate solid forms that are milled may have a water content of more, or less, than about 5 weight percent. Under this meaning, an intermediate solid form having a water content of more than about 5 weight percent may be milled, with the resulting granules being further dried to a water content of less than about 5 weight percent. In addition, under this meaning, an intermediate solid form having a water content of less than about 5 weight percent may be milled, with additional drying of the resulting granules either being, or not being, necessary to produce samples of PCC composition having a water content of less than about 5 weight percent, depending on the distribution of water content in the intermediate solid form before milling.

In addition, "bulk density" is to be distinguished from simple "density." As used herein, "bulk density" refers to the weight or mass of a granulated or powdered form of PCC composition per tapped gross volume of the granulated or powdered form. Tapped gross volume is the sum of the volume of particles (granular or powdered) themselves in the granulated or powdered form of the PCC composition plus the volume of interparticle interstices, after the container (e.g., a graduated cylinder) holding the granulated or powdered form of the PCC composition is tapped to settle the particles of the PCC composition. Furthermore, "high bulk density" as used herein means a bulk density that is from about 0.8 g/cc to about 1.3 g/cc for such tapped granulated or powdered form of the PCC composition.

As used herein, "administering a composition" or "administering the composition" means administering to a subject a PCC composition either directly in tablet or other solid form, or indirectly as a beverage after dissolving a solid form of a PCC composition in a liquid. Typically, such a composition is orally administered so that the subject receives beneficial mineral supplementation. The subject may be human, or a nonhuman animal subject. A subject in need of such a composition may simply, or additionally, be a subject susceptible to kidney-stone formation. Target dosages for administering a PCC composition to a human subject, for example, are set so that a subject receives from about 0.5 gram to about 2.0 grams calcium daily. Target dosages for administering such a composition to a nonhuman animal subject, on the other hand, are adjusted, for example, based on the body mass of the animal.

As used herein, "unit dosage form" means one tablet or other type of solid form composition comprising high bulk density potassium calcium citrate as a single compound—in 1:1:1, or 4:1:2, respectively, molar ratio—suitable for administration as, for example, one lozenge, one chewable tablet, or one capsule (or spoonful measure) containing granulated or powdered forms. Each "dosage unit" may be administered directly in tablet or other solid form, or, indirectly as a beverage, after dissolving a tablet or other solid form composition comprising high bulk density potassium calcium citrate as a single compound—in 1:1:1, or 4:1:2, respectively, molar ratio—in a liquid. Administration is preferably oral.

The following examples are included to demonstrate preferred embodiments of the invention. It should be appreciated by those of skill in the art that the techniques disclosed in the following examples represent techniques discovered by the inventor to function well in the practice of the invention, and thus can be considered to constitute preferred modes for its practice. However, those of skill in the art should, in light of the present disclosure, appreciate that, while changes can be made in specific techniques disclosed, yet like or similar results may be obtained without departing from the spirit and scope of the invention.

EXAMPLE 1

Tablets of PCC Composition (1:1:1 Molar Ratio)

Citric acid (120 g, 0.625 moles) powder and water (30 g) were thoroughly mixed in a large beaker. Calcium oxide (35.0 g, 0.624 moles) was added with rapid stirring. Potassium carbonate (43.2 g, 0.313 moles) powder was introduced in four approximately equal portions, each portion added after the carbon dioxide ($CO_2$) evolution had slowed or ceased. Water (10 g) was added to complete the reaction. After drying, the material was sized and found to have a bulk density slightly greater than 1.1 g/cc. Bulk density was determined by an Archimedean method. This dense granulated form of PCC composition (1:1:1 molar ratio) was subjected to compression tableting with the aid of a binder and lubricant. Tablets of PCC composition (1:1:1 molar ratio) providing 5 meq potassium (about 195 mg), 10 meq calcium (about 200 mg), and 15 meq citrate (about 945 mg) were produced.

Tablets of PCC composition (1:1:1 molar ratio) were also produced on a large scale. Citric acid (48.03 kg, 250 moles) powder and water (10 kg) were placed in a Colton 3 cu. ft. ribbon mixer and blended for two minutes. Calcium oxide (14.02 kg, 250 moles) was added in approximately three equal portions, three minutes apart with continuous mixing. Potassium carbonate (17.3 kg, 125 moles) was added in approximately three equal portions five minutes apart with continuous mixing. Water (10 kg) is added in order to complete the reaction. Mixing continued for 2–5 minutes. The resulting granular material was placed on trays and dried at 150° F. (66° C.) for six hours. The dried product was sized and its bulk density was determined to be about 1.1 g/cc. The sizing was done using a Fitzmill Model No. 6 mill equipped with a 3162AA screen.

The dried granulated form of PCC composition (1:1:1 molar ratio) was subjoined with 1.0 weight percent magnesium stearate, and 10 weight percent carnauba wax. The composition was then tableted in a multiple station tablet press to form tablets of PCC composition (1:1:1 molar ratio) each providing at least about 195 mg potassium, 200 mg calcium, and 945 mg citrate. Multiple station tablet presses such as a Colton #216–16 station press, a Vector #247–41 station press, or a Manesty rotopress-37 station press, for example, may be used. The tablets thus obtained may be final products or may be further processed.

Further processing to improve these tablets physically and aesthetically may be accomplished by tablet-coating procedures well known to those skilled in relevant pharmaceutical arts in light of the present disclosure. For example, a coating comprising hydroxypropylmethylcellulose, titanium dioxide, and talc was placed on these tablets. This coating procedure was by conventional pharmaceutical pan-coating technology.

EXAMPLE 2

PCC Composition (1:1:1 Molar Ratio) Produced Using Calcium Carbonate

Procedure of Example 1 for large-scale production was followed with the calcium oxide being replaced by calcium carbonate (25.03 kg, 250 moles). A granulated PCC composition comprising PCC in 1:1:1 molar ratio and having a bulk density of about 1.05 g/cc was produced.

EXAMPLE 3

PCC Composition (1:1:1 Molar Ratio) Produced Using Calcium Hydroxide

Procedure of Example 1 for large-scale production was followed with the calcium oxide being replaced by calcium hydroxide (18.52 kg, 250 moles). A granulated PCC composition comprising PCC in 1:1:1 molar ratio and having a bulk density of about 1.05 g/cc was produced.

EXAMPLE 4

PCC Composition (1:1:1 Molar Ratio) Produced Using Potassium Bicarbonate

The procedures of Examples 1, 2, and 3 are followed using potassium bicarbonate instead of potassium carbonate. However, since the mole amount of potassium in a mole of potassium bicarbonate is half the mole amount of potassium in a mole of potassium carbonate, the mole amount of potassium bicarbonate (250 moles, or 25.03 kg) used is twice the mole amount of potassium carbonate (125 moles) used in Examples 1, 2, and 3. A granulated PCC composition comprising PCC in 1:1:1 molar ratio and having a bulk density of about 1.05 g/cc is produced.

EXAMPLE 5

PCC Composition (1:1:1 Molar Ratio) Produced Using Potassium Hydroxide

The procedures of Examples 1, 2, and 3 are followed using potassium hydroxide instead of potassium carbonate. However, since the mole amount of potassium in a mole of potassium hydroxide is half the mole amount of potassium in a mole of potassium carbonate, the mole amount of potassium hydroxide (250 moles, or 14.03 kg) used is twice the mole amount of potassium carbonate (125 moles) used in Examples 1, 2, and 3. A granulated PCC composition comprising PCC in 1:1:1 molar ratio and having a bulk density of about 1.05 g/cc is produced.

EXAMPLE 6

PCC Composition (4:1:2 Molar Ratio)

Citric acid (120 g, 0.625 moles) powder and water (30 g) are thoroughly mixed in a large beaker. Calcium oxide (17.5 g, 0.312 moles) is added with rapid stirring. Potassium carbonate (86.4 g, 0.625 moles) powder is introduced in four approximately equal portions, each portion added after the $CO_2$ evolution had slowed or ceased. Water (10 g) is added to complete the reaction. After drying, the material is sized and found to have a bulk density between 0.9 and 1.3 g/cc. Bulk density is determined by an Archimedean method. This dense granulated form of PCC composition comprising high bulk density PCC in 4:1:2, respectively, molar ratio is subjected to compression tableting with the aid of a binder and lubricant, and tablets providing 10 meq potassium (about 391 mg), 5 meq (about 100 mg) calcium, and 15 meq (about 945 mg) citrate are produced.

Tablets of PCC composition (4:1:2 molar ratio) may also be produced on a large scale. Citric acid (24.01 kg, 125 moles) powder and water (5 kg) are placed in a Colton 3 cu. ft. ribbon mixer and blended for two minutes. Calcium oxide (3.51 kg, 62.5 moles) is added in approximately three equal portions, three minutes apart with continuous mixing. Potassium carbonate (17.28 kg, 125 moles) is added in approximately three equal portions five minutes apart with continuous mixing. Water (5 kg) is added in order to complete the reaction. Mixing is continued for 2–5 minutes. Resulting granular material is placed in trays and dried at 150° F. (66° C.) for six hours. The dried product is sized using a Fitzmill Model No. 6 mill equipped with a 3162AA screen.

PCC composition (4:1:2 molar ratio) may also be produced using the preceding large-scale procedure with calcium oxide being replaced by calcium carbonate (6.26 kg, 62.5 moles) or calcium hydroxide (4.63 kg, 62.5 moles). Similarly, PCC composition (4:1:2 molar ratio) may be produced using the preceding large-scale procedure with potassium carbonate being replaced by potassium bicarbonate (25.0 kg, 250 moles) or potassium hydroxide (14.03 kg, 250 moles).

The dried composition comprising high bulk density PCC as a single compound in 4:1:2, respectively, molar ratio is subjoined with 1.0 weight percent magnesium stearate, and 10 weight percent carnauba wax. The resulting composition is then tableted in a multiple station tablet press to form tablets of PCC composition (4:1:2 molar ratio) wherein each tablet provides about 391 mg potassium, about 100 mg calcium, and about 945 mg citrate. Multiple station tablet presses such as a Colton #216–16 station press, a Vector #247–41 station press, or a Manesty rotopress-37 station press, for example, may be used. The tablets thus obtained may be final products or may be further processed. Further processing to improve these tablets physically and aesthetically may be accomplished by tablet-coating procedures well known to those skilled in relevant pharmaceutical arts in light of the present disclosure, as noted in the previous examples for PCC composition (1:1:1 molar ratio).

EXAMPLE 7

Physiological Studies Comparing PCC Composition to Calcium Citrate

The present example provides physiological studies in which 500 mg calcium was administered orally in the form of tablets of PCC composition (1:1:1 molar ratio) or tablets of calcium citrate to each of six volunteers. The calcium citrate administered was a dense tablet form of calcium citrate (i.e., ULTRADENSE™ CITRACAL® comprising calcium citrate having a molar ratio of calcium to citrate of 3:2, respectively) as described in U.S. Pat. No. 4,814,177 (previously incorporated by reference). The volunteers were characterized as physiologically "normal." Each subject underwent three phases of study in random order, with each phase corresponding to a separate "calcium load" test. In one test, tablets of PCC composition (1:1:1 molar-ratio) providing 500 mg (25 meq) calcium, 12.5 meq potassium, and 37.5 meq citrate (that is, tablets of PCC composition providing 12.5 mmoles each of potassium, calcium, and citrate) were orally administered to each subject after an overnight fast. In separate tests, tablets of calcium citrate (providing 500 mg, i.e., 25 meq, calcium and 25 meq citrate), or placebo (containing only excipient) were also administered to each subject. Before each administration or load, a two-hour fasting urine sample (Control) was collected. Four hours after each load, a urine sample (Experimental) was again collected. A venous blood sample was taken just before (Control) and at four hours after (Experimental) the load.

Figure 1:
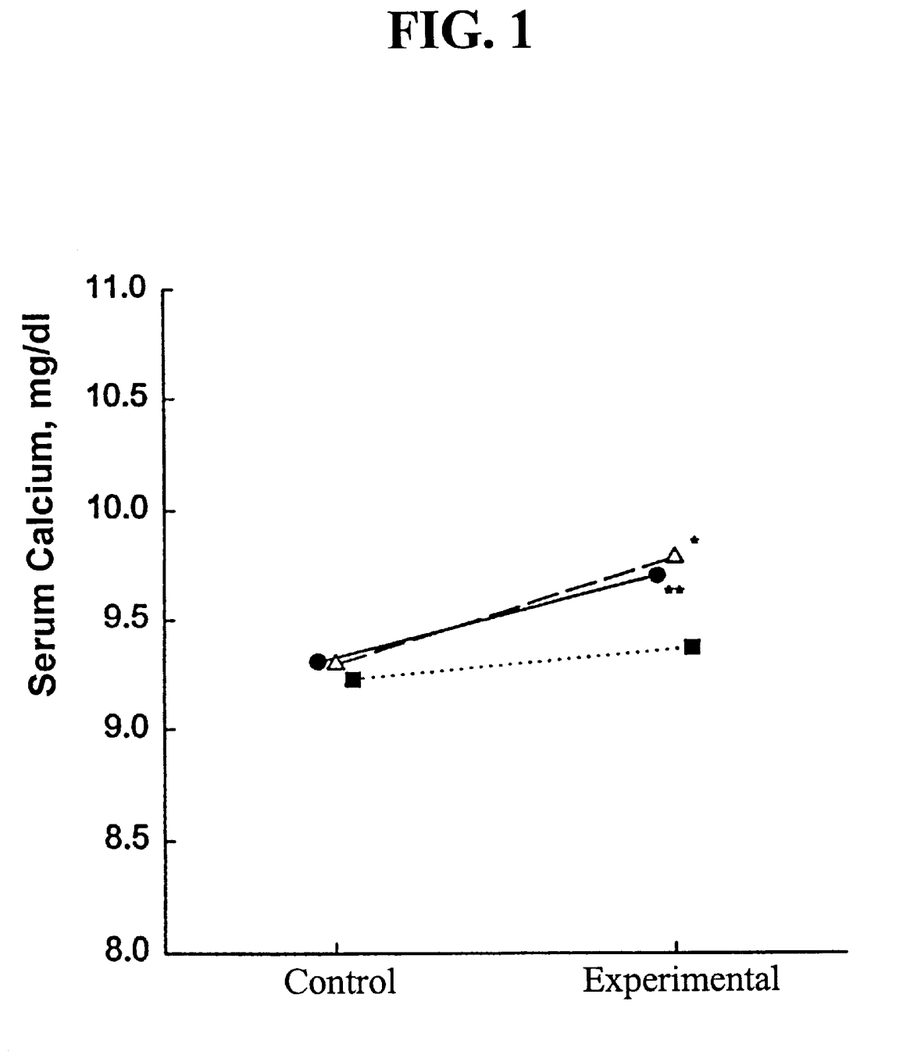
FIG. 1. Effect of PCC composition, calcium citrate, and placebo on serum calcium (mg/dl).
Figure 3:
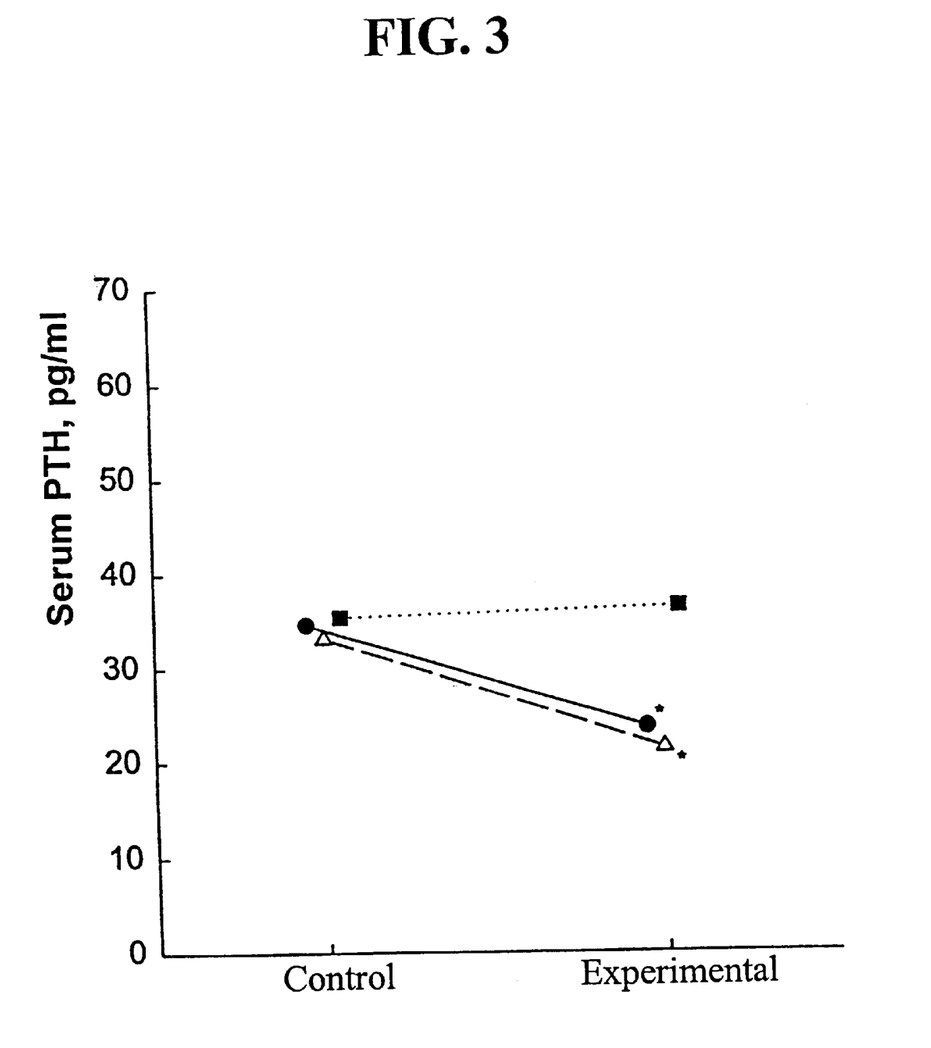
FIG. 3. Effect of PCC composition, calcium citrate, and placebo on serum PTH (pg/ml).

In order to determine levels of serum calcium (FIG. 1) and serum parathyroid hormone (PTH) (FIG. 3), measurements were made directly of the venous blood samples obtained just before (Control) and at four hours after (Experimental) treatment administration. Measured values were expressed in units of milligrams per deciliter (mg/dl) and picograms per milliliter (pg/ml) for serum calcium and serum PTH levels, respectively.

Figure 2:
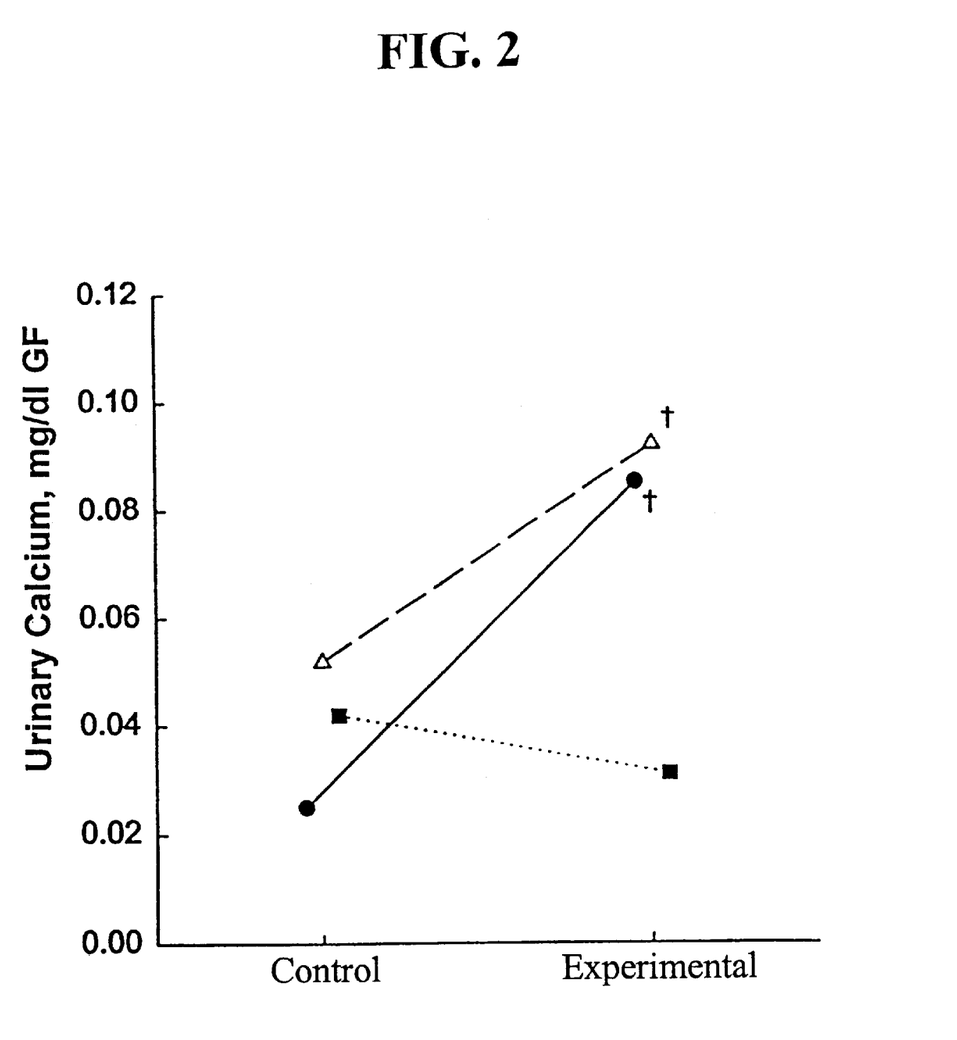
FIG. 2. Effect of PCC composition, calcium citrate, and placebo on urinary calcium (mg/dl GF).
Figure 4:
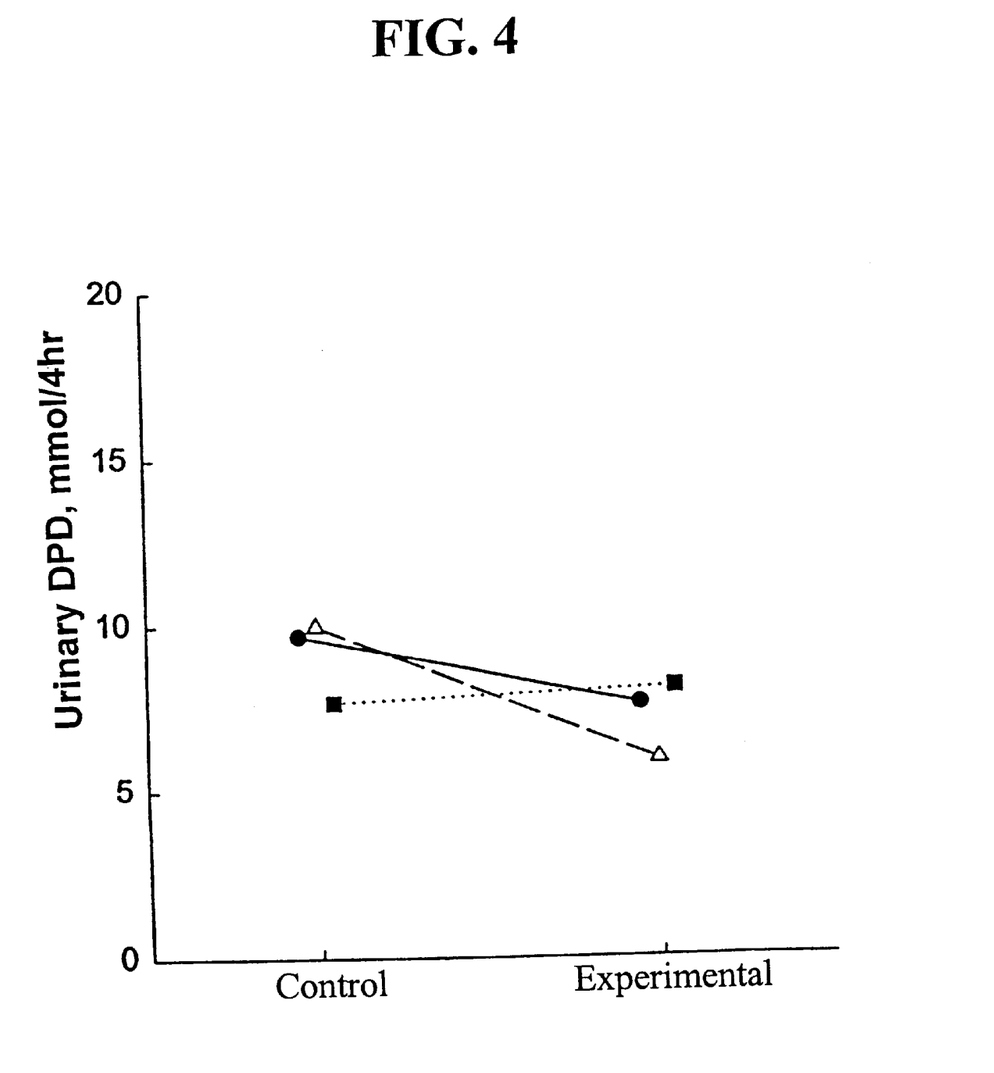
FIG. 4. Effect of PCC composition, calcium citrate, and placebo on urinary DPD (mmol/4hr).
Figure 5:
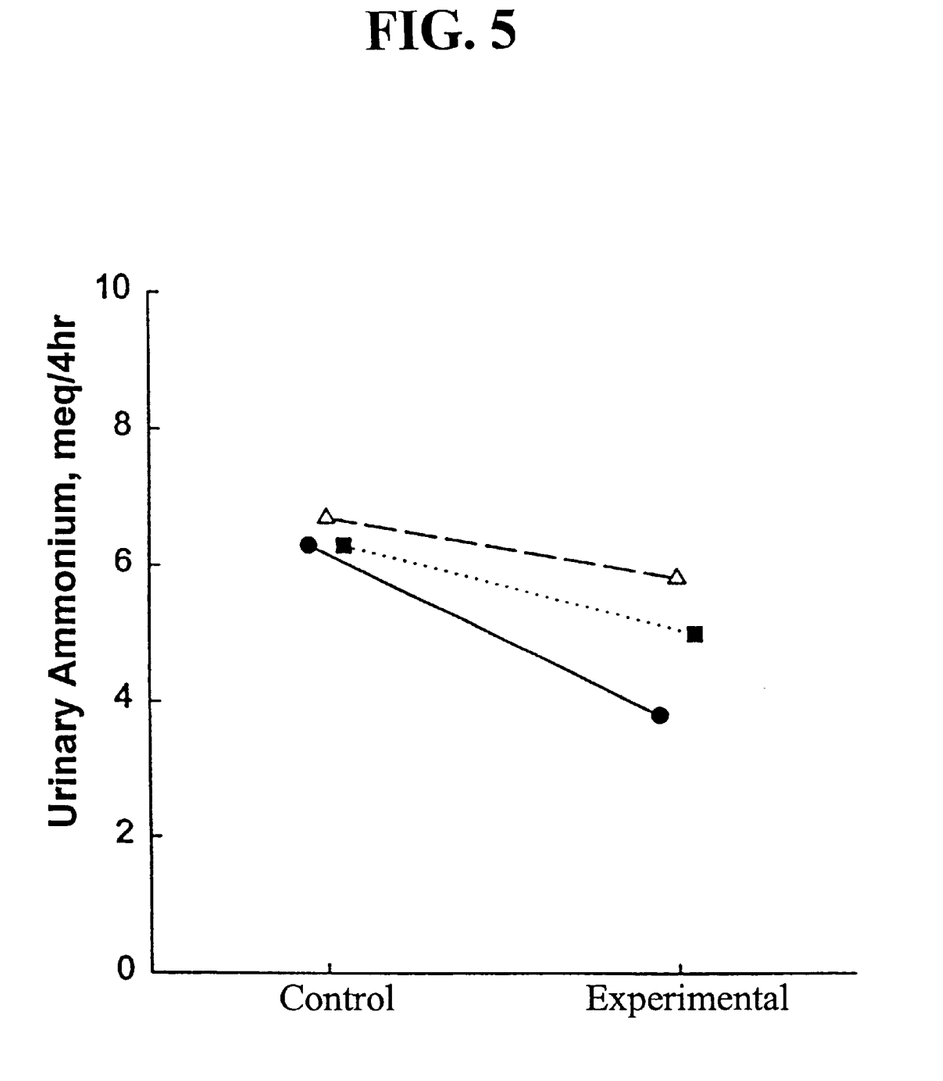
FIG. 5. Effect of PCC composition, calcium citrate, and placebo on urinary ammonium (meq/4hr).
Figure 6:
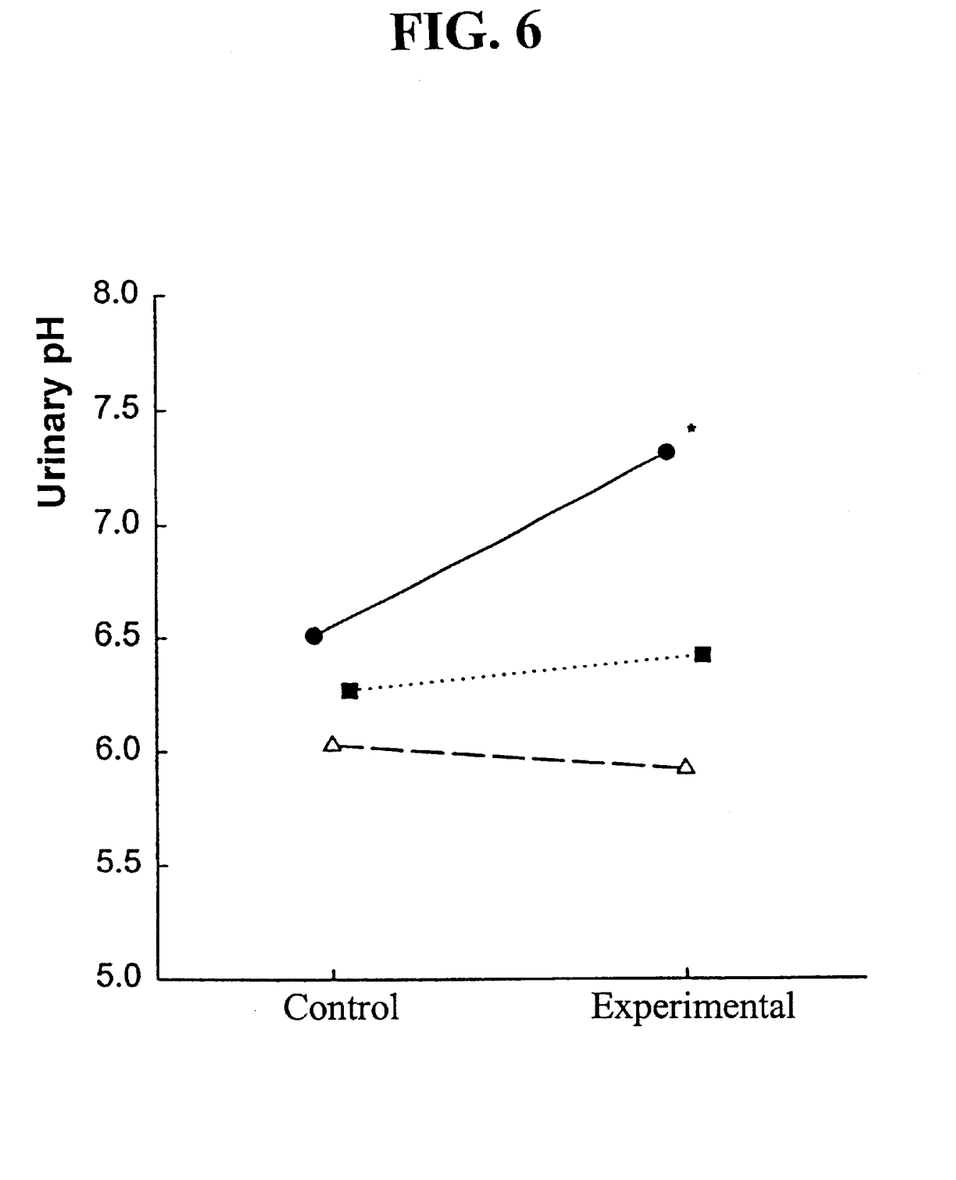
FIG. 6. Effect of PCC composition, calcium citrate, and placebo on urinary pH.
Figure 7:
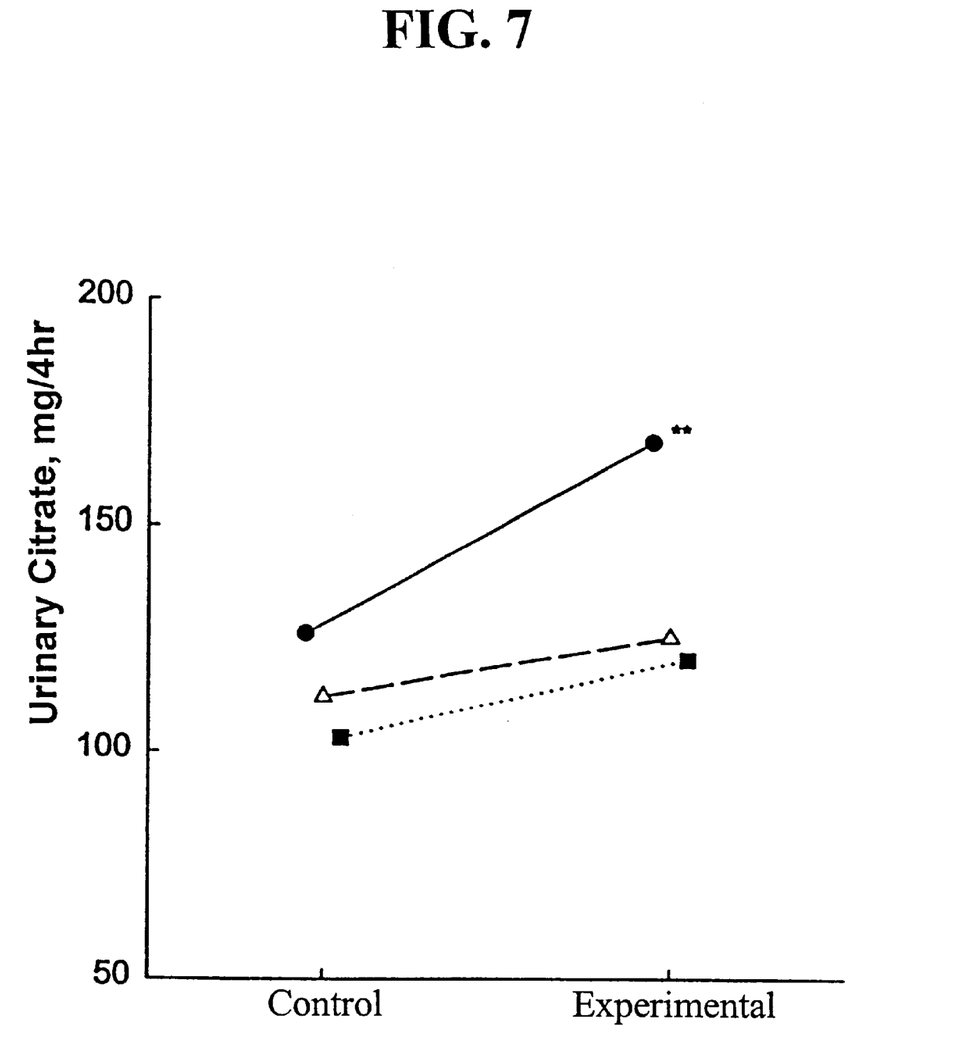
FIG. 7. Effect of PCC composition, calcium citrate, and placebo on urinary citrate (mg/4hr).

Urine samples were measured for creatinine, as well as for calcium, deoxypyridinoline (DPD), ammonium, pH, and citrate. Urinary calcium (FIG. 2) levels were measured directly from two-hour fasting urines (Control) and from urines collected four hours after (Experimental) treatment administration; measured values were expressed in units of milligrams per deciliter glomerular filtrate (mg/dl GF). Measured values for pH (FIG. 6) are independent of volume. Urinary DPD (FIG. 4) levels were expressed as millimoles per four hours (mmol/4hr); urinary ammonium (FIG. 5) levels were expressed in units of milliequivalents per four hours (meq/4hr); and urinary citrate (FIG. 7) levels were expressed in units of mg per four hours (mg/4hr). Measurements were taken from two-hour fasting urines and from urines collected four hours after (Experimental) treatment administration. In order to estimate Control values for urinary DPD, ammonium, and citrate in units of mmol/4hr (DPD), meq/4hr (ammonium), or mg/4hr (citrate), values measured from two-hour fasting urines were multiplied by two to obtain four-hour Control values. Measurements from urine samples collected four hours after treatment administration were used, without adjustment, as Experimental values.

Levels of serum calcium (FIG. 1) and urinary calcium (FIG. 2) did not appreciably change after administration of placebo, but increased after administration of PCC composition and calcium citrate. Significantly higher experimental values were obtained on administration of PCC composition or calcium citrate than on administration of placebo, but between PCC composition and calcium-citrate administrations, experimental values for serum calcium levels did not significantly differ. Thus, administering 500 mg calcium in the form of either tablets of PCC composition or tablets of calcium citrate significantly enhanced the amount of calcium absorbed from GI tracts of the subjects.

Levels of serum PTH (FIG. 3) remained substantially constant after administration of placebo, but decreased after administration of either PCC composition or calcium citrate. Significantly lower experimental values of serum PTH were obtained on administration of PCC composition or calcium citrate than on administration of placebo, but experimental values were not significantly different between PCC composition and calcium-citrate administrations. Thus, PCC composition was shown to be as effective as calcium citrate in suppressing PTH secretion and thereby would be expected to be effective in inhibiting bone destruction.

Levels of urinary DPD (FIG. 4), a marker for bone destruction, did decrease after administration of either PCC composition or calcium citrate. However, experimental values of urinary DPD obtained on administration of either PCC composition or calcium citrate did not decrease significantly versus those values obtained on administration of placebo.

Levels of urinary ammonium (FIG. 5) decreased non-significantly on administration of PCC composition, calcium citrate, or placebo. Experimental values of urinary ammonium obtained on administration of PCC composition were lower than those obtained on administration of placebo, but experimental values obtained on administration of calcium citrate were not. Consistent with these trends, but of statistical significance, urinary pH (FIG. 6) increased significantly on administration of PCC composition, but not on administration of either calcium citrate or placebo. Experimental values of urinary pH obtained on administration of PCC composition were significantly higher those obtained on administration of placebo, but those obtained on administration of calcium citrate were not. Thus, experimental values of urinary pH indicated that, during the four hours after loading, administration of PCC composition delivered alkali load, but calcium-citrate administration did not. More specifically, the provision by administration of PCC composition, versus calcium-citrate administration, of a greater net increase in urinary pH demonstrated that administration of PCC composition delivered a more-than-modest level of alkali load.

Levels of urinary citrate (FIG. 7) also markedly increased on administration of PCC composition, but not on administration of either calcium citrate or placebo. Experimental values of urinary citrate obtained on administration of PCC composition were significantly greater than those obtained on administration of placebo, while those obtained on administration of calcium citrate were not. Thus, during the four hours after loading, administration of PCC composition enhanced urinary citrate excretion, but calcium-citrate administration did not. Administration of PCC composition likely increases urinary citrate excretion both by providing citrate that escapes in vivo metabolism and by delivering a more-than-modest level of alkali load. However, as for potassium citrate, the profound citraturic action of PCC composition is likely attributable predominantly to its delivery of alkali load.

EXAMPLE 8

Dietary Supplementation and Methods of Treatment

A subject who may benefit from dietary supplementation with a PCC composition, or an alcohol-mixed composition, is identified. For example, a human (or nonhuman animal) subject susceptible to the development of osteoporosis or bone loss, or who has already suffered osteoporosis or bone loss, is identified using diagnostic indicators, for example, such as the subject's age, sex, bone density, history of fractures, or steroid therapy experience. Such a subject would also be identified as potentially benefiting from dietary supplementation with a PCC composition. Similarly, a human (or nonhuman animal) subject having, or susceptible to, conditions other than osteoporosis in which calcium administration may be therapeutic, including hypoparathyroidism, renal osteodystrophy, hypertension, bone loss in chronic diarrheal syndrome, osteomalacia, rickets, and phosphate accumulation in chronic renal failure, is identified. Such a human (or nonhuman animal) subject would also be identified as potentially benefiting from dietary supplementation with a PCC composition.

PCC composition is administered to a human subject in need thereof so that the subject receives beneficial mineral supplementation, for example, from about 0.5 gram to about 2.0 grams calcium daily. Typically, a tablet of PCC composition (1:1:1 molar-ratio) contains 200 mg calcium, so that a human subject would ingest from 2 to 10 tablets daily. A tablet of PCC composition (4:1:2 molar-ratio) typically contains 100 mg calcium, so that a human subject would ingest from 5 to 20 tablets daily. Administration is preferably oral, and may proceed either directly by ingesting a solid form, such as a tablet, or indirectly by drinking liquid in which a solid form, such as a tablet, has been dissolved.

Administration of a PCC composition to a nonhuman animal subject is accomplished using administration techniques available from veterinary medicine in light of the present disclosure.

Administration of PCC composition to a subject provides calcium and, simultaneously, delivers a more-than-modest level of alkali load. The latter is also manifested by an increase in urinary pH. The alkali load delivered helps to avert, for example, development of osteoporosis or bone loss, and/or helps to counter osteoporosis or bone loss already suffered (for example, in a postmenopausal woman or an elderly man). Administration of PCC composition as dietary supplement also reduces the risk of nephrolithiasis (i.e., kidney-stone formation) through provision of increases in urinary pH and citraturic effect, as well as, at least potentially, by providing potassium instead of sodium.

What is claimed is:

1. A composition useful as a dietary supplement to provide potassium, calcium, and citrate, said composition comprising potassium calcium citrate as a single compound having a bulk density from about 0.8 grams per cubic centimeter to about 1.3 grams per cubic centimeter, wherein potassium, calcium, and citrate in the single compound are in a molar ratio of 1:1:1.

2. The composition of claim 1 wherein said composition has a bulk density ranging between about 0.9 g/cc to about 1.3 g/cc.

3. The composition of claim 1 wherein said composition has a bulk density ranging between about 0.9 glcc to about 1.1 g/cc.

4. The composition of claim 1 wherein said composition is in a unit dosage form so as to deliver about 5 meq potassium, about 10 meq calcium, and about 15 meq citrate in each dosage unit.

5. A composition useful as a dietary supplement to provide potassium, calcium, and citrate, said composition comprising potassium calcium citrate as a single compound having a bulk density from about 0.8 grams per cubic centimeter to about 1.3 grams per cubic centimeter, wherein potassium, calcium, and citrate in the single compound are in a molar ratio of 4:1:2, respectively.

6. The composition of claim 5 wherein said composition has a bulk density ranging between about 0.9 glcc to about 1.3 g/cc.

7. The composition of claim 5 wherein said composition has a bulk density ranging between about 0.9 g/cc to about 1.1 g/cc.

8. The composition of claim 5 wherein said composition is in a unit dosage form so as to deliver about 10 meq potassium, about 5 meq calcium, and about 15 meq citrate in each dosage unit.

9. The composition of claim 1 wherein the moisture content of said composition is less than about five weight percent.

10. The composition of claim 5 wherein the moisture content of said composition is less than about five weight percent.

11. A composition comprising potassium calcium citrate as a single compound having the chemical formula $KCa(OOCCH_2COHCOOCH_2COO)$ and where the potassium calcium citrate compound has a bulk density from about 0.8 grams per cubic centimeter to about 1.3 grams per cubic centimeter.

12. A composition comprising potassium calcium citrate as a single compound having the chemical formula $K_4Ca(OOCCH_2COHCOOCH_2COO)_2$ and where the potassium calcium citrate compound has a bulk density from about 0.8 grams per cubic centimeter to about 1.3 grams per cubic centimeter.

13. A process for producing a composition having a water content of less than about 5 weight percent, said composition comprising potassium calcium citrate as a single compound having a bulk density from about 0.8 grams per cubic centimeter to about 1.3 grams per cubic centimeter, wherein potassium, calcium, and citrate in the single compound are in a molar ratio of 1:1:1, the process comprising the steps of:

mixing citric acid, a calcium compound, and water to form a first mixture wherein citric acid and calcium are in approximately 1:1 molar ratio;

adding a potassium compound to form a second mixture wherein potassium and citric acid are in approximately 1:1 molar ratio and the second mixture has a water content of between about 10 weight percent and about 75 weight percent; and drying and milling said second mixture to a water content of less than about 5 weight percent to produce the compsition.

14. The process of claim 13 wherein the composition has a bulk density between about 0.9 g/cc and about 1.1 g/cc.

15. A composition produced by the process of claim 13.

16. A composition produced by the process of claim 14.

17. A process for producing a composition having a water content of less than about 5 weight percent, said composition comprising potassium calcium citrate as a single compound having a bulk density from about 0.8 grams per cubic centimeter to about 1.3 grams per cubic centimeter, wherein potassium, calcium, and citrate in the single compound are in a molar ratio of 4:1:2, respectively, the process comprising the steps of:

mixing citric acid, a calcium compound, and water to form a first mixture wherein citric acid and calcium are in approximately 2:1 molar ratio, respectively;

adding a potassium compound to form a second mixture wherein potassium and citric 5 acid are in approximately 2:1 molar ratio, respectively, and the second mixture has a water content of between about 10 weight percent and about 75 weight percent; and drying and milling said second mixture to a water content of less than about 5 weight percent to produce the composition.

18. The process of claim 17 wherein the composition has a bulk density between about 0.9 g/cc and about 1.1 g/cc.

19. A composition produced by the process of claim 17.

20. A composition produced by the process of claim 18.

21. The process of claim 13 wherein the second mixture has a water content of between about 10 weight percent and about 25 weight percent.

22. The process of claim 21 wherein the calcium compound is selected from the group consisting of calcium oxide, calcium carbonate, calcium hydroxide, and mixtures thereof.

23. The process of claim 22 wherein the calcium compound is calcium oxide.

24. The process of claim 22 wherein the calcium compound is calcium carbonate.

25. The process of claim 22 wherein the calcium compound is calcium hydroxide.

26. The process of claim 21 wherein the potassium compound is selected from the group consisting of potassium carbonate, potassium hydroxide, potassium bicarbonate, and mixtures thereof.

27. The process of claim 26 wherein the potassium compound is potassium carbonate.

28. The process of claim 17 wherein the second mixture has a water content of between about 10 weight percent and about 25 weight percent.

29. The process of claim 28 wherein the calcium compound is selected from the group consisting of calcium oxide, calcium carbonate, calcium hydroxide, and mixtures thereof.

30. The process of claim 29 wherein the calcium compound is calcium oxide.

31. The process of claim 29 wherein the calcium compound is calcium carbonate.

32. The process of claim 29 wherein the calcium compound is calcium hydroxide.

33. The process of claim 28 wherein the potassium compound is selected from the group consisting of potassium carbonate, potassium hydroxide, potassium bicarbonate, and mixtures thereof.

34. The process of claim 33 wherein the potassium compound is potassium carbonate.

35. A method for providing potassium, calcium, and citrate to a subject in need thereof, the method comprising the step of administering the composition of claim 1 to the subject.

36. A method for providing potassium, calcium, and citrate to a subject in need thereof, the method comprising the step of administering the composition of claim 5 to the subject.

37. A method for delivering a more-than-modest level of alkali load to a subject in need thereof, the method comprising the step of administering the composition of claim 1 to the subject.

38. A method for delivering a more-than-modest level of alkali load to a subject in need thereof, the method comprising the step of administering the composition of claim 5 to the subject.

39. A method for countering osteoporosis in a subject in need thereof, the method comprising the step of administering the composition of claim 1 to the subject.

40. A method for countering osteoporosis in a subject in need thereof, the method comprising the step of administering the composition of claim 5 to the subject.

41. A method for countering bone loss in a subject in need thereof, the method comprising the step of administering the composition of claim 1 to the subject.

42. A method for countering bone loss in a subject in need thereof, the method comprising the step of administering the composition of claim 5 to the subject.

43. A method for simultaneously countering bone loss and kidney-stone formation in a subject in need thereof, the method comprising administering the composition of claim 1 to the subject.

44. A method for simultaneously countering bone loss and kidney-stone formation in a subject in need thereof, the method comprising administering the composition of claim 5 to the subject.

* * * * *

UNITED STATES PATENT AND TRADEMARK OFFICE
CERTIFICATE OF CORRECTION

PATENT NO. : 6,287,607 B2  
APPLICATION NO. : 09/356649  
DATED : September 11, 2001  
INVENTOR(S) : Charles Y. C. Pak et al.

Page 1 of 1

It is certified that error appears in the above-identified patent and that said Letters Patent is hereby corrected as shown below:

In column 18, line 5, delete "glcc" and insert --g/cc--.

In column 18, line 19, delete "glcc" and insert --g/cc--.

Signed and Sealed this
Tenth Day of May, 2011

David J. Kappos
*Director of the United States Patent and Trademark Office*